United States Patent [19]

Burton

[11] 4,381,765
[45] May 3, 1983

[54] ILEOSTOMY VALVE

[75] Inventor: Thomas A. Burton, Rochester, Minn.

[73] Assignee: Waters Instruments, Inc., Rochester, Minn.

[21] Appl. No.: 250,231

[22] Filed: Apr. 2, 1981

[51] Int. Cl.³ ............................................. A61B 19/00
[52] U.S. Cl. .................................... 128/1 R; 604/98; 604/277; 604/335
[58] Field of Search ............... 128/1 R, 227, 239, 245, 128/246, 283, 348–350 R, DIG. 26

[56] References Cited

U.S. PATENT DOCUMENTS

| 1,710,701 | 4/1929 | Hertzberg | 128/227 |
| 1,810,466 | 6/1931 | Deutsch | 128/348 |
| 1,888,349 | 11/1932 | Jacoby | 128/349 R |
| 2,586,940 | 2/1952 | Graham | 128/349 R |
| 3,253,594 | 5/1966 | Matthews et al. | 128/348 |
| 3,802,418 | 4/1974 | Clayton | 128/283 X |
| 3,828,782 | 8/1974 | Polin | 128/283 |
| 4,119,100 | 10/1978 | Rickett | 128/350 R |

Primary Examiner—Dalton L. Truluck
Attorney, Agent, or Firm—James R. Haller

[57] ABSTRACT

An ileostomy valve for controlling bowel continence. The valve includes drainage tube means having a flexible outer end portion and an inner end portion, securing means carried by the inner end portion for securing the latter to the stoma of a patient deep to the fascia, and means for releasably sealing the outer end portion of the drainage tube. The latter means comprises means carried by the drainage tube means for releasably retaining the outer end thereof in a collapsably folded position along its length to form a waterproof seal.

10 Claims, 15 Drawing Figures

ILEOSTOMY VALVE

TECHNICAL FIELD

The invention relates to the field of medical prosthetic devices, particularly those devices intended for use with ileostomy or cholostomy patients.

BACKGROUND ART

Bowel diseases and abnormal conditions, including particularly cancer of the lower bowel, have led to surgical operations commonly referred to as ileostomies or cholostomies in which a portion of the bowel is removed and the end of the remaining bowel is brought out through the patient's abdomen. The lower bowel may terminate at the surface of the abdominal skin, or, more commonly, may protrude slightly from the outer skin surface, the bowel passing through the abdominal fascia, muscle, fat and skin layers. The end portion of the bowel, extending to or through the skin, is referred to as the stoma. Patients who have had such surgical operations commonly are provided with externally worn containers such as plastic bags, the bags having an opening that is adhesively sealed to the skin about the stoma. A short tube may be anchored at one end within the stoma, with its outer end extending outwardly for attachment to a receptacle, and tubes of this type are shown in U.S. Pat. Nos. 3,828,782 and 4,119,100. The bowel is thus continually open to the flow of its contents through the stoma and into the bag. Such bags must be periodically removed and emptied, of course, and the adhesive seal of the mouth of the bag to the skin surrounding the stoma must be maintained airtight to prevent the escape of odors and consequent embarrassment to the wearer. If disposable bags are used, means must be found for properly disposing of the bag with their contents. Further, the skin area surrounding the stoma must be maintained very clean, and irritations due to the adhesive seal between the skin and mouth of the bag must be avoided.

Depending largely upon the diet of the patient, the bowel contents issuing from the stoma is characterized by a soupy, watery consistency, and the bowel contents may include particles of undigested or partially digested food, all of which must be permitted to escape from the stoma. Thus, it is desirable that the stoma be kept as free as possible of devices interferring with the flow of the bowel contents.

U.S. Pat. No. 3,447,533 shows a device that is inserted within the stoma and is retained therein to permit the wearer some control over bowel functions for the purpose of eliminating the necessity of an externally worn bag or other receptacle. Other devices have been employed to provide urinary continence, such devices including interior valves which can be opened or closed. Typical of such devices are those shown in U.S. Pat. Nos. 3,642,004, 3,758,073 and 3,812,841. With ileostomy devices, of course, interior valves or other obstructions interferring with the flow of bowel contents should be avoided.

DISCLOSURE OF INVENTION

The invention provides an ileostomy valve having no interior obstructions interferring with the free flow of bowel contents from the valve. The valve includes a drainage tube having an inner end portion insertable within the stoma of a patient and having a flexible outer end portion. Securing means carried by the inner end portion are provided to secure the latter to the stoma deep to the fascia. Means also are provided for releasably sealing the outer end portion of the drainage tube means, such means comprising means carried by the tube means for shaping and for releasably retaining the flexible outer end portion of the tube in a bent, collapsed, desirably double-back orientation to form a waterproof seal and carrying the valve flatly adjacent the skin of a patient.

BEST MODE FOR CARRYING OUT THE INVENTION

Figure 1:
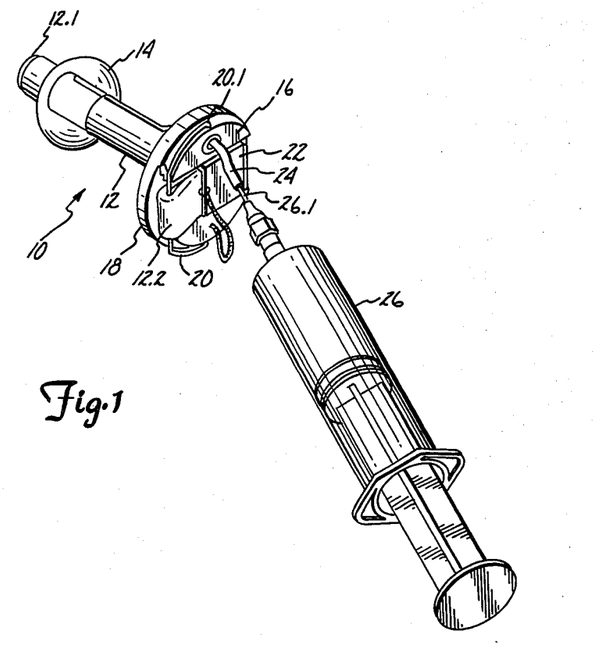
FIG. 1 is a perspective view of the ileostomy valve of the invention, shown attached to a syringe employed in anchoring the valve within the stoma of a patient.
Figure 2:
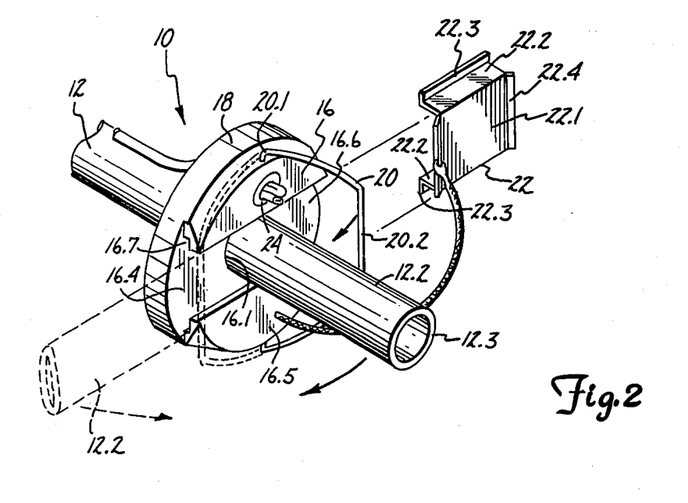
FIG. 2 is a broken-away, perspective view of the valve of FIG. 1.

Referring first to FIG. 1, the ileostomy valve of the invention is designated generally as 10, and includes drainage tube means typified as drainage tube (12); means, depicted as balloon (14) for securing or anchoring the inner end (12.1) of the tube within the stoma of a patient deep to the fascia; and a valve body (16) worn exteriorly of the patient and including means for releasably sealing the flexible upper end portion (12.2) of the drainage tube. The drainage tube is shown in its open position in FIG. 2, permitting the bowel contents to be discharged from its outer end (12.2), and is shown in its sealed position in FIGS. 3, 4 and 5. The interior of the drainage tube means is free of obstructions preventing the free flow of bowel contents when the valve is in its open position as shown in FIG. 2.

As in common with prosthetic devices, the sizes of valves of the invention may be varied to accommodate different patients. It will thus be understood that the dimensions typified below are for illustrative purposes only.

The drainage tube (12) desirably is made of a physiologically acceptable material such as silicone rubber, and may be on the order of 10–15 cm in length with an outer diameter of about 13 mm and an inner diameter of about 10 mm. Although it is desirable that the tube be flexible along its entire length, the inner end portion (12.1) of the tube may be more rigid, if desired. The outer end portion (12.2), however, must be sufficiently flexible so as to be able to be folded back upon itself tightly to provide a liquid-tight and air-tight seal. As initially provided to a patient, the drainage tube may be somewhat longer than needed, and may be trimmed by the patient or physician to the proper length for that patient. At least the outer, flexible end of the drainage tube preferably has a frictional outer surface; that is, when the flexible end (12.2) of the drainage tube is folded back upon itself so that its outer surfaces are touching, the surface characteristics of the tube should be such as to permit the surfaces to slide upon one another only with difficulty. Commercial silicone rubber tubing of the type commonly employed for medical usage has suitable characteristics of physiological acceptability and frictional outer surfaces.

The valve body (16), representative of means for releasably sealing the outer end portion of the drainage tube, preferably is generally disc-shaped and is provided with a central aperture (16.1) through which the outer, flexible end portion of the drainage tube (12) snugly passes. The diameter of the aperture (16.1) preferably is slightly less than the outer diameter of the drainage tube (12) so that the position of the valve body (16) along the tube (12) is restrained by friction between the tube and valve body. The inner surface (12.2) of the valve body, which is the surface facing the skin "S" of the patient when the ileostomy valve is worn, may be provided with an annular groove (16.3) within which is retained a resilient retaining ring (18), the latter having a portion extending from the surface (16.2) of the valve body to provide a circular cushion between the valve body and the skin. The cushion should protrude from the valve body a sufficient distance to preferably space the valve body slightly away from the skin of the wearer, and may be made of any resilient material such as foam rubber or the like. Good results have been obtained by using a cushion formed of a short length of small diameter silicone tubing, the tubing being joined end-to-end with an airtight seal so that it is air-tight. Different sized cushions, of course, can be employed to accommodate the varying skin softness, fat layers and the like of different patients. A ring or cushion of silicone rubber, as above-described, and having an outer diameter of about 6 mm has been found to be effective. Inasmuch as such silicone rubber tubing can be deformed as needed to be seated in the annular groove (16.3), the valve of the invention may be provided with several such rings having varying tubing diameters so that the most comfortable ring may be employed by the wearer.

With reference to the embodiment shown in FIGS. 1–5, the valve body (16) has an elongated groove (16.4) cut into its outer surface (16.5), that is, the surface facing away from the patient's skin when the device is worn. The groove (16.5) intersects the aperture (16.1) through the valve body, and the edges of the groove (16.4) adjacent the floor (16.6) thereof are undercut to provide recessed channels (16.7).

A bail, (20) desirably made of wire and having a generally U-shaped configuration, is provided with inwardly turned ends (20.1) that are journaled into small holes provided for that purpose in opposite edges of the valve body (16), the connection of the bail ends with the valve body permitting the bail to swing from side to side across the front surface (16.5) of the valve body in line with the elongated groove (16.4) formed in the valve body, as shown best in FIG. 2. The central portion (20.2) of the bail (20) is generally straight and has an outer surface or edge that extends across the groove (16.4) generally normal to the length of the groove.

Referring to FIG. 2, the outer end portion (12.2) of the drainage tube extends outwardly of the valve body (16) through the aperture (16.1). When the tube is to be sealed to prevent the flow of bowel contents therethrough, the outer end portion of the tube is bent so that it collapses, the inner walls of the tube sealingly engaging to provide a waterproof and air-tight seal. Although any degree of bend that collapses the tube to this extent will suffice, it is preferred to bend the tube through about 180°, that is, to double the tube back upon itself into the position shown is phantom lines in FIG. 2. The central portion (20.2) of the bail is swung into contact with the tube end portion, as also shown in phantom lines in FIG. 2. The tube end portion (12.2) is then doubled back upon itself over the central bail portion (20.2) into the position shown in FIG. 5. By being in this manner collapsed and doubled over upon itself, the bend or crease that is provided in the drainage tube provides the tube with a waterproof and air-tight seal, preventing the escape of bowel contents. The central portion (20.2) of the bail thus typifies means presenting a surface generally normal to the length of the tube and over which the outer end portion of the tube may be bent to form a waterproof seal.

Figures 3, 4, 5:
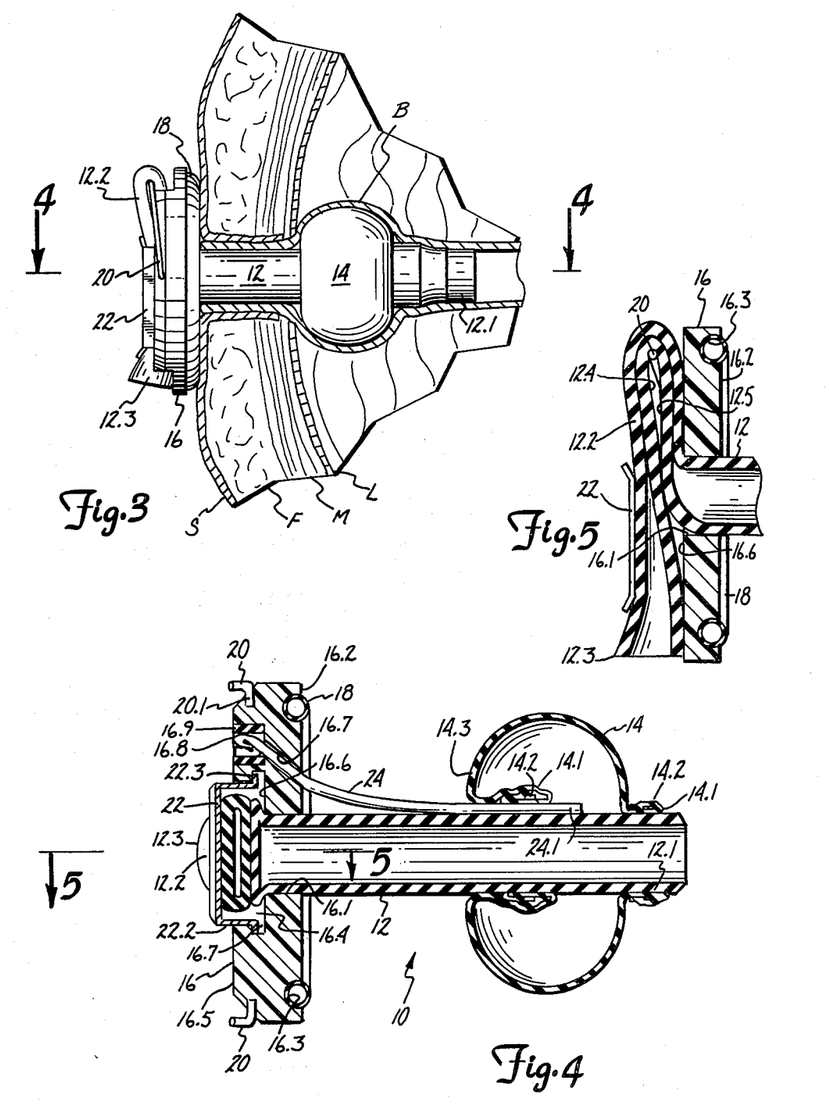
FIG. 3 is a cross-sectional view of the device of FIG. 2, showing the same in its closed or sealed position and secured within the stoma of a patient.
FIG. 4 is a cross-sectional view taken along line 4—4 of FIG. 3.
FIG. 5 is a broken-away, cross-sectional view taken along line 5—5 of FIG. 4.
Figure 6:
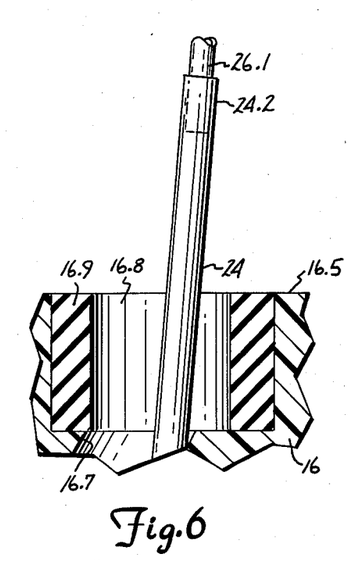
FIG. 6 is a broken-away, cross-sectional view of a portion of the valve shown in FIG. 4.

Retaining means, typified by the clamp (22) in FIG. 5, are provided to releasably maintain the outer end portion (12.2) of the tube in its doubled-back position. The clamp (22) is generally U-shaped in cross-section, and has a generally flat top or cover portion (22.1) and generally parallel side walls (22.2) terminating in outwardly turned flanges (22.3), the latter flanges fitting into the undercut channels (16.7) of the valve body as shown best in FIG. 4. Once the outer end portion of the drainage tube has been doubled back upon itself about the central portion of the bail, as shown in FIG. 5, the retaining clamp or bracket (22) is urged over the free end (12.3) of the drainage tube, the flanges (22.3) of the retaining clamp sliding within the undercut channels (16.7) of the valve body and the top or cover portion (22.1) of the clamp contacting and pressing inwardly upon the outer end portion of the drainage tube to retain it in the bent-over position. A tether (22.4) (FIG. 2) of flexible material, may be used to prevent the loss of the clamp (22).

Referring particularly to FIG. 5, it will be noted that the confronting outer surfaces (12.4, 12.5) of the drainage tube on either side of the bail (20) are maintained in frictional contact with each other when the clamp (22) is in place. Such frictional contact stabilizes the contacted portions of the drainage tube with respect to each other and thus prevents the valve body (16) from slipping outwardly along the drainage tube. Further, as shown particularly in FIGS. 3, 4 and 5, the valve (10), when in its closed or sealed position, lies rather flatly adjacent the abdomen of the wearer to avoid interference with the wearer's clothing.

Referring now to FIGS. 1 and 4, the inner end portion of the drainage tube is provided with an inflatable, balloon-like structure (14) typifying means for securing the inner end of the drainage tube within the stoma of the patient deep to the fascia of the patient. The balloon may be formed from a length of thin-walled tubing, preferably silicone rubber tubing, with the ends (14.1) of the tubing being cemented circumferentially to the outer surface of the drainage tube as shown in FIG. 4. Additional bands of tubing, designated (14.2), may be employed to more securely hold the ends of the tubing forming the balloon to the outer surface of the drainage tube. By appropriately tensioning the tubing forming the balloon-like structure, the balloon, when inflated, may assume the configuration shown in FIG. 4, the outwardly or forwardly facing surface (14.3) of the balloon rising sharply from the circumferential outer surface of the drainage tube.

Figure 7:
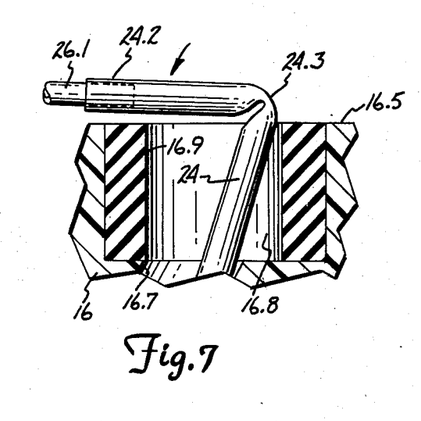
FIG. 7 is a broken-away, cross-sectional view similar to that of FIG. 6 but showing a step in the anchoring of the device within the stoma of a patient.
Figure 8:
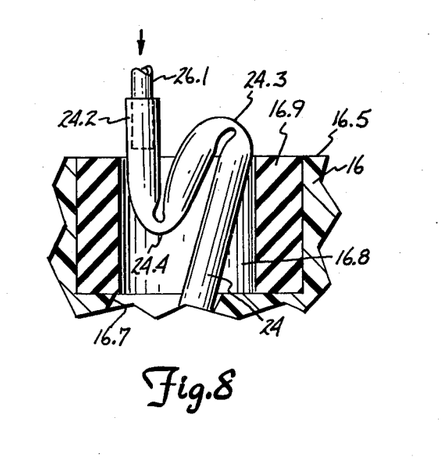
FIG. 8 is a broken-away, cross-sectional view similar to that of FIG. 7 but showing a further step in the process of securing the device within the stoma of a patient.
Figure 9:
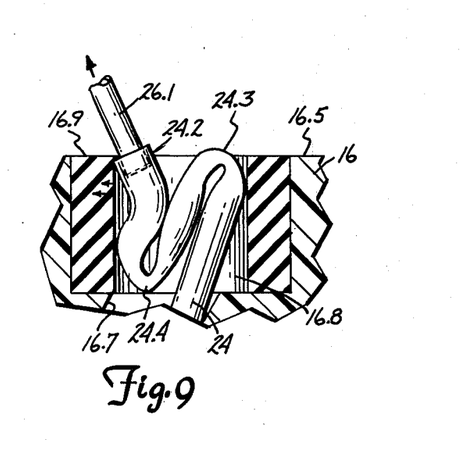
FIG. 9 is a broken-away, cross-sectional view similar to that of FIGS. 6–8 and showing another step in said process.

A small inflation tube (24) desirably also of silicone rubber, extends from within the balloon structure (14) forwardly along the outer surface of the drainage tube and passes snugly through an oblique orifice (16.71) formed through the valve body to the exterior of the valve body. As noted in FIGS. 4 and 6–9, the oblique orifice (16.71) formed in the valve body expands abruptly within the valve body to an orifice of greater diameter designated (16.8), the latter orifice extending to the outer, front surface (16.5) of the valve body. The orifice (16.8) is lined along its side with a short length of high friction tubing (16.9) such as silicone rubber tubing. The balloon structure (14) is inflated through the inflation tube (24) by means of a pump typified by a small hypodermic syringe (26) (FIG. 1) equipped with a short, smooth-nosed needle (26.1). Water preferably is used to inflate the balloon structure (14). The needle (26.1) is snugly inserted into the open outer end (24.2) of the inflation tube, and the plunger is depressed to inflate the balloon structure. To seal the end of the inflation tube, the needle (26.1) is bent downwardly as shown in FIG. 7 to cause a crease or crimp (24.3) to be formed in the tube. The needle is then maneuvered as shown in FIG. 8 to force a loop of the inflation tube inwardly of the orifice (16.8), this maneuver causing a second crimp (24.4), spaced from the first crimp, to form, the crimps (24.3, 24.4) thus sealing the inflation tube against the escape of water from the balloon structure (14). Finally, with the outer end (2.22) of the inflation tube positioned within the orifice (16.8), the needle is tilted as shown in FIG. 9 and is withdrawn along the edge of the tubular liner (16.9), the liner restraining outward movement of the inflation tube end (24.2) and permitting the needle to be disengaged from the inflation tube. The frictional forces developed between the outer surfaces of the inflation tube as it contacts itself in the "S"-shaped bend within the orifice (16.8), and the contact of the inflation tube walls with the inner walls of the tubular liner (16.9), restrain the inflation tube end from escaping from the orifice (16.8).

Figure 10:
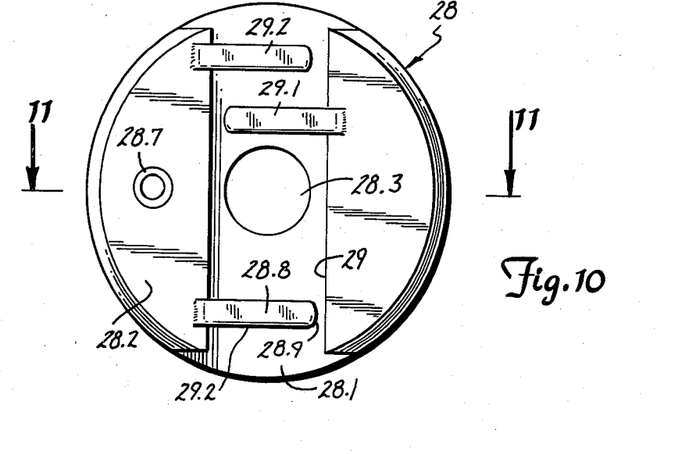
FIG. 10 is a plan view of a modified valve body of a valve of the invention.
Figure 11:
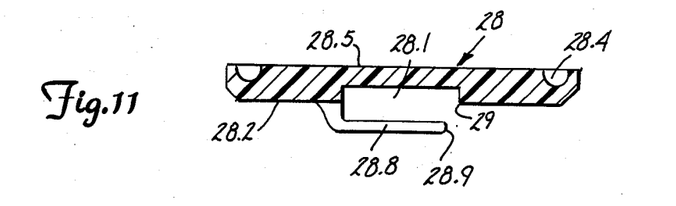
FIG. 11 is a cross-sectional view taken along line 11—11 of FIG. 10.
Figure 12:
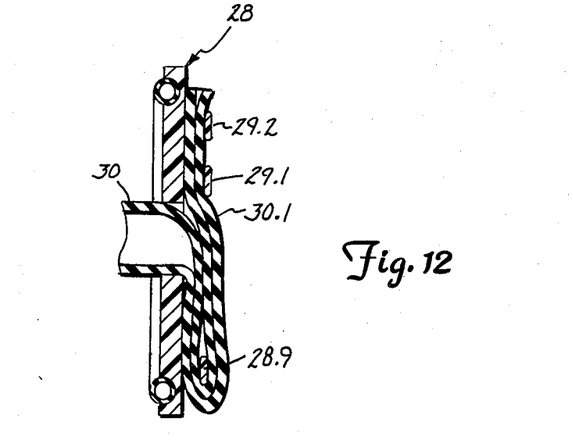
FIG. 12 is a cross-sectional view, partially broken away, of a valve using the valve body of FIGS. 10 and 11.

Another embodiment of the valve body, designated (16) in the foregoing description, is shown as (28) in FIGS. 10–12. The generally disc-shaped valve body (28) is provided with a central slot (28.1) across its outer surface (28.2), the slot intersecting an aperture (28.3) formed centrally through the valve body to receive the flexible outer end portion (30.1) of a drainage tube (30) identical to the drainage tube (12) described above. As with the above-described valve body (16), the valve body (28) is provided with an annular groove (28.4) formed in its rearward or skin-facing surface (28.5) and within which can be seated a cushioning ring (28.6). An inflation tube orifice (28.7) similarly is formed through the thickness of the valve body.

From the outer surface (28.2) of the valve body adjacent one end of the slot (28.1) arises a finger-like projection (28.8), typifying shaping means, this projection extending outwardly and then across the slot (28.1). The end (28.9) of the finger is spaced from the adjacent wall (29) of the slot by a sufficient distance to permit the flexible outer end (30.1) of the drainage tube to be pinched flat and slipped sideways between the end of the finger and the adjacent wall (29) to nest in the slot (28.1).

Similar fingers (29.1, 29.2) arise from the outer surface (28.2) of the valve body on the other side of the aperture (28.3) at opposite sides of the slot (28.1), and extend across the slot as shown in FIG. 10. The latter fingers are spaced from one another, and their ends are spaced from the respective side walls of the slot to enable the outer, flexible end portion (30.1) of the drainage tube to be pinched flat along its length and slipped sideways beneath the fingers into the slot (28.1).

In the thus described embodiment of FIGS. 10–12, the flexible outer end portion (30.1) of the drainage tube is sealed by first bending it toward the finger (28.8), inserting it sideways beneath this finger, doubling the end of the tube back upon itself so as to form a bend about the finger (28.8), and pinching the tube flat along its length and slipping it sideways first beneath the finger (29.1) and then beneath the finger (29.2). Note that confronting outer frictional surfaces of the drainage tube are maintained in frictional contact with one another as shown best in FIG. 12. The outermost edge (29.2) (FIG. 10) of the finger (28.8) serves as an edge or narrow surface over which the flexible outer end of the drainage tube can be collapsibly bent and folded back upon itself.

Figure 13:
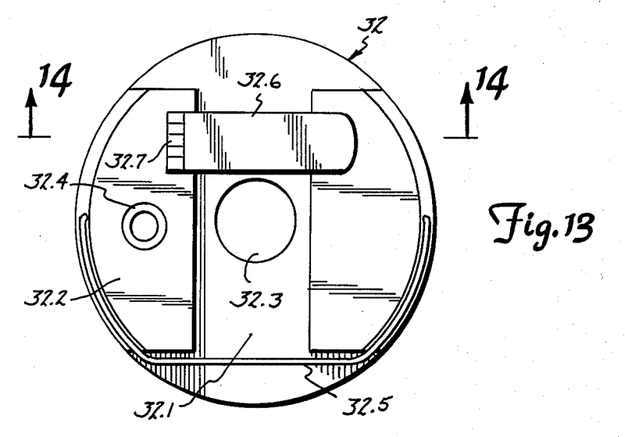
FIG. 13 is a plan view of another modified valve body of a valve of the invention.
Figure 14:
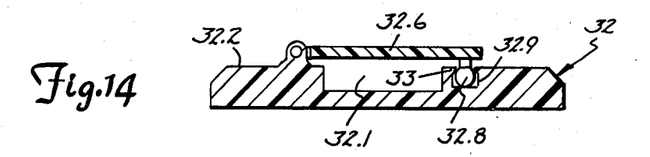
FIG. 14 is a cross-sectional view taken along line 14—14 of FIG. 13.
Figure 15:
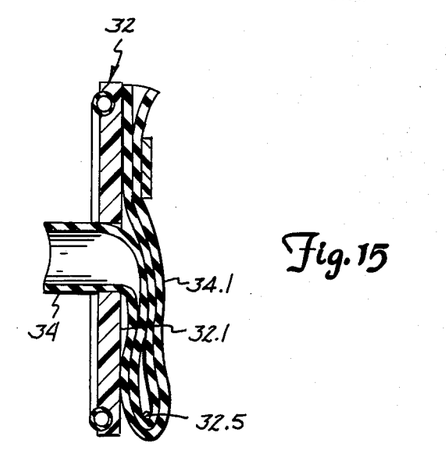
FIG. 15 is a cross-sectional view, partially broken away, of a valve using the valve body of FIGS. 13 and 14.

Another modification of the valve body is designated (32) in FIGS. 13–15. As described previously, the valve body (32) is generally disc-shaped and is provided with a slot (32.1) along its outer surface (32.2), the slot intersecting the central aperture (32.3) formed through the thickness of the valve body. A drainage tube orifice (32.4) is provided in the manner described above. A generally U-shaped bail (32.5) has its ends rotatably journaled into the sides of the valve body, as described above in connection with, for example, FIG. 2.

Retaining means in the form of a gate fastener, designated generally as (32.6) extends across the slot (32.1) near one end thereof, one end of the gate (32.6) being pivotally connected to the outer surface (32.2) of the valve body by a hinge (32.7). At its other end, a ball fastener (32.8) (FIG. 14) protrudes from the gate (32.6) and is received within a recess (32.9) formed in the outer surface (32.2) of the valve body. The walls of the recess (32.9) may converge slightly near the rim (33) thereof so that the opening provided by the rim is very slightly smaller than the ball coupling (32.8), thereby permitting the ball coupling to be snapped into the recess to hold the gate (32.6) in its closed position as shown in FIG. 14.

The bail (32.5) is employed in the same manner as has been described above in connection with the embodiment of FIGS. 1–5. When the flexible outer end portion (34.1) of the drainage tube (34) has been doubled back upon itself about the generally straight, central section of the bail (32.5), it is then nested in the slot (32.1) and the gate (32.6) is swung over the doubled back portion and is snapped in place to retain the doubled back portion of the tube in the slot (32.1).

The drainage valve of the invention may be prepared for use by applying an appropriate lubricant to the inner end (12.1) of the drainage tube and to the outer surfaces of the inflated balloon structure so that the same can be easily inserted within the stoma of a patient. The outer end of the drainage tube (12) extends forwardly through the valve body (18), as shown in FIG. 2, and the inflation tube extends forwardly through the orifices (16.71), (16.8) formed in the valve body. The inner end (12.1) of the drainage tube is then inserted into the stoma of a patient, care being taken that the balloon structure is deep, that is, internal, to the abdominal fascia of the patient. As shown in FIG. 3, a patient's skin is depicted as "S", the underlying layer of fat as "F", the underlying muscular layer by "M" and the fascia, the extremely strong inner lining of the abdomen, by "L". Once the inner end (12.1) of the drainage tube has been sufficiently deeply inserted into the stoma, the balloon structure (14) is inflated by means of the hypodermic syringe (26). It is desired to employ water in the amount of about 10-25 cc as the inflation medium. When inflated, the balloon structure occupies the position shown generally in FIG. 3, the balloon distending the bowel as depicted and thus anchoring the inner end (12.1) of the drainage tube from escaping through the hole formed in the fascia "L" during the ileostomy operation. The fascia, it must be understood, is an extremely tough membrane and easily is able to bear the pressure of the distended bowel "B" pushing forwardly upon it; in this manner, the inner end (12.1) of the drainage tube is firmly anchored within the stoma of the patient.

After inflation of the balloon structure (14), the drainage tube (12) is pulled firmly forwardly to securely seat the distended portion of the bowel "B" against the fascia, and the valve body (16) is then drawn rearwardly along the drainage tube until it seats securely against the skin of the patient, as shown in FIG. 3. During this operation, the inflation tube (24) is also drawn forwardly through the valve body orifices (16.71), (16.8) to avoid premature kinking of the inflation tube. When the valve body has been securely but comfortably positioned against the skin of the patient, the flexible outer end (12.2) of the drainage tube is bent over into the position shown in phantom lines in FIG. 2, the bail (20) is brought down upon the folded over portion of tubing, and the tubing is doubled back on itself and secured with the retaining clamp (22) as described above. This operation seals the outer end of the drainage tube against the escape of bowel contents, and further anchors the valve body (16) to the drainage tube in relation to the balloon structure (14). Finally, the outer end of the inflation tube, which will have been previously cut to the correct length, is doubled back upon itself within the orifice (16.8) as described above in connection with FIGS. 6-9, and the needle (26.1) is removed. A slight excess length of the inflation tube is permitted to occupy the space between the valve body and the skin of the patient so that the valve body may be readjusted along the length of the drainage tube without permitting the balloon structure (14) to become deflated.

When it is desired to empty the bowel, the patient merely removes the retaining clamp (22) and, pinching the drainage tube shut at its outer end (12.3), permits the drainage tube to assume the position shown in FIG. 2. Releasing the end (12.3) of the drainage tube permits the bowel contents to be drained. When drainage is completed, the inside of the drainage tube is swabbed clean. If readjustment of the valve body is believed to be required, an outward pull on the outer end of the drainage tube (12) is maintained while the valve body is snugged up against the skin of the wearer, following which the outer end of the drainage tube is again sealed by being folded back upon itself and clamped in place, all as described above.

It will be particularly noted that when the outer, flexible end of the drainage tube is in its open position, as shown in FIG. 2, the tube is free of inner obstructions preventing or interferring with the free flow of bowel contents. There is no inner valve mechanism that may fail or become clogged. Yet, the valve when in its sealed position as shown in FIG. 5, is fully sealed against the accidental escape of waste material or gas from the stoma. In its sealed position, the valve is worn flat against the abdomen and does not unduly interfere with the activities of the patient. Depending upon the location of the stoma in the abdomen of the patient, the stoma may be substantially completely hidden from view even when brief clothing such as bathing suits are worn, thereby greatly reducing phychological trauma to the patient.

It will be understood that various modifications may be made to the invention without departing from the spirit thereof nor the scope of the claims. For example, other means may be provided to enable the outer, flexible end of the drainage tubing to be folded back upon itself and retained in place, and other means may be found for retaining the inner end of the drainage tube in an anchored position within the stoma deep to the fascia of a patient.

While a preferred embodiment of the present invention has been described, it should be understood that various changes, adaptations and modifications may be made therein without departing from the spirit of the invention and the scope of the appended claims.

What is claimed is:

1. An ileostomy valve connectable to the stoma of a patient for controlling continence, and including
   a drainage tube having an inner end portion insertable within the stoma of a patient and having a flexible outer end portion, the tube being free of internal obstructions interfering with the free flow of bowel contents from the valve;
   securing means carried by the inner end portion for securing the latter to the stoma deep to the facia;
   means for releasably sealing the outer end portion of the drainage tube and comprising means carried by the tube exterior of the patient for releasably shaping the flexible outer end portion of the drainage tube in a bent collapsed orientation to seal the tube and means retaining and carrying said tube in said bent orientation flatly adjacent the skin of a patient.

2. The valve of claim 1 in which said means carried by the tube exteriorly of the patient comprises plate means having an orifice through which the flexible outer end portion of the drainage tube passes, the plate means being adjustable along the flexible outer end portion of the drainage tube to hold the plate means tightly against the skin of the patient.

3. The ileostomy valve of claim 1 in which the flexible end portion of the drainage tube has a frictional friction outer surface, and wherein said means for releasably retaining the outer end portion of the drainage tube in a bent collapsed orientation maintains contact between the outer surfaces of the tube on either side of the bend to restrain movement of the drainage tube with respect to the sealing means.

4. The ileostomy valve of claim 2 in which said means for releasably securing the outer end portion of the drainage tube in its bent collapsed orientation comprises means releasably attachable to the plate means and having a bearing surface holding the bent portion of the drainage tube against the plate means.

5. The ileostomy valve of claim 2 in which the means releasably securing the outer end portion of the drainage tube in its bent collapsed orientation comprises hook means carried by the plate means and beneath which the bend-over portion of the drainage tube means may be releasably hooked.

6. An ileostomy valve connectable to the stoma of a patient for controlling continence, and including
- a drainage tube having an inner end portion insertable within the stoma of a patient and having a flexible outer end portion, the tube being free of internal obstructions interfering with the free flow of bowel contents from the valve.
- securing means carried by the inner end portion of the drainage tube for securing the latter to the stoma deep to the facia;
- valve body means having an inner surface contactable with the patient's skin and having an orifice through which extends the flexible outer end portion of the drainage tube; and
- means for releasably sealing the outer end portion of the drainage tube including means carried by the valve body means and presenting an edge over which the outer end portion of the drainage tube may be collapsibly bent and doubled back upon itself against the valve body to form a waterproof seal, and means for releasably securing the outer end portion in its doubled-back position to carry the same flatly adjacent the skin of a patient.

7. An ileostomy valve connectable to the stoma of a patient for controlling continence, and including
- a drainage tube having an inner end portion insertable within the stoma of a patient and having a flexible outer end portion;
- securing means carried by the inner end portion of the drainage tube for securing the latter to the stoma deep to the facia;
- valve body means having an inner surface contactable with the patient's skin and having an orifice through which extends the flexible outer end portion of the drainage tube; and
- means for releasably sealing the outer end portion of the drainage tube including a generally U-shaped wire bail pivotally secured at its ends to the valve body and having a generally straight central portion defining an edge over which the outer end portion of the drainage tube may be collapsibly bent and doubled back against itself to form a waterproof seal, and means for releasably securing the outer end portion in its doubled back position.

8. The ileostomy valve of claim 7 including a generally U-shaped retaining clamp having outwardly directed flanges, and wherein the valve body includes an elongated slot formed therein intersecting the orifice, the slot having parallel, elongated, opposed recesses therein oriented to receive the retaining clamp flanges.

9. The ileostomy valve of claim 7 wherein the valve body includes an elongated slot formed therein intersecting the orifice, and gate means hingedly connected at one end to the valve body and extending over the slot adjacent one end thereof, the gate means having, at its other end, attachment means for releasably attaching the latter end of the gate means to the valve body to releasably secure the outer end portion of the drainage tube in its double-back position.

10. An ileostomy valve connectable to the stoma of a patient for controlling continence, and including
- a drainage tube having an inner end portion insertable within the stoma of a patient and having a flexible outer end portion, the tube being free of internal obstructions interfering with the free flow of bowel contents from the valve;
- securing means carried by the inner end portion for securing the latter to the stoma deep to the facia; and
- means for releasably sealing the outer end portion of the drainage tube and comprising means carried by the tube exterior of the patient for releasably shaping the flexible outer end portion of the drainage tube in a bent, collapsed orientation to provide a waterproof seal, and means retaining and carrying said tube in said bent orientation with portions thereof on either side of the bend laying generally normal to the inner end portion of the drainage tube, whereby the valve may be carried flatly against the patient's skin.

* * * * *